US012115240B2

(12) United States Patent
Taylor et al.

(10) Patent No.: US 12,115,240 B2
(45) Date of Patent: Oct. 15, 2024

(54) GEL STABILIZED O/W EMULSION WITH ALPHA-ARBUTIN AND AZELAIC ACID DISPERSION

(71) Applicant: L'OREAL, Paris (FR)

(72) Inventors: Alison Nicole Taylor, Jersey City, NJ (US); Maggie Su, Cranford, NJ (US); Patricia Brieva, Manalapan, NJ (US); Stephen Matthew Lynch, Westfield, NJ (US)

(73) Assignee: L'OREAL, Paris (FR)

( * ) Notice: Subject to any disclaimer, the term of this patent is extended or adjusted under 35 U.S.C. 154(b) by 118 days.

(21) Appl. No.: 17/187,084

(22) Filed: Feb. 26, 2021

(65) Prior Publication Data

US 2022/0273543 A1 Sep. 1, 2022

(51) Int. Cl.
| | | |
|---|---|---|
| *A61K 8/81* | (2006.01) | |
| *A61K 8/31* | (2006.01) | |
| *A61K 8/362* | (2006.01) | |
| *A61K 8/37* | (2006.01) | |
| *A61K 8/49* | (2006.01) | |
| *A61K 8/60* | (2006.01) | |
| *A61Q 19/00* | (2006.01) | |

(52) U.S. Cl.
CPC ............... *A61K 8/602* (2013.01); *A61K 8/31* (2013.01); *A61K 8/362* (2013.01); *A61K 8/37* (2013.01); *A61K 8/4926* (2013.01); *A61K 8/8111* (2013.01); *A61K 8/8188* (2013.01); *A61Q 19/00* (2013.01); *A61K 2800/30* (2013.01); *A61K 2800/34* (2013.01); *A61K 2800/48* (2013.01); *A61K 2800/5424* (2013.01); *A61K 2800/5922* (2013.01)

(58) Field of Classification Search
None
See application file for complete search history.

(56) References Cited

U.S. PATENT DOCUMENTS

| | | | |
|---|---|---|---|
| 4,595,586 A | 6/1986 | Flom | |
| 5,378,461 A | 1/1995 | Neigut | |
| 5,814,313 A * | 9/1998 | Slavtcheff | A61K 8/891 |
| | | | 424/78.02 |
| 6,524,598 B2 | 2/2003 | Sunkel et al. | |
| 7,349,857 B2 | 3/2008 | Manzo | |
| 8,034,755 B2 | 10/2011 | Kawano | |
| 9,442,494 B2 | 9/2016 | Igarashi | |
| 9,913,790 B2 * | 3/2018 | Cropper | A61K 8/37 |
| 9,978,931 B2 | 3/2018 | Dersh et al. | |
| 10,231,911 B2 | 3/2019 | Dersh et al. | |
| 2002/0128621 A1 * | 9/2002 | Kruchoski | A61K 8/731 |
| | | | 604/385.01 |
| 2006/0088496 A1 | 4/2006 | McManus et al. | |
| 2006/0118005 A1 * | 6/2006 | Hardy | C09J 123/0853 |
| | | | 106/600 |
| 2006/0275332 A1 * | 12/2006 | Agarwal | A61K 8/042 |
| | | | 424/401 |
| 2007/0082017 A1 | 4/2007 | Tseng | |
| 2008/0243523 A1 | 10/2008 | Beilis | |
| 2009/0022826 A1 | 1/2009 | Shrier et al. | |
| 2009/0074685 A1 * | 3/2009 | Lai | A61K 8/31 |
| | | | 424/59 |
| 2009/0263340 A1 * | 10/2009 | Ille-Boehler | A61K 8/676 |
| | | | 514/161 |
| 2011/0158922 A1 | 6/2011 | Dupont et al. | |
| 2011/0305737 A1 | 12/2011 | Alexiades-Armenakas | |
| 2013/0317108 A1 * | 11/2013 | At | A61K 47/32 |
| | | | 514/569 |
| 2014/0179640 A1 * | 6/2014 | Weinberger | C07C 279/14 |
| | | | 514/159 |
| 2015/0021356 A1 | 1/2015 | Witchell et al. | |
| 2015/0238405 A1 * | 8/2015 | Wu | A61K 8/19 |
| | | | 424/63 |
| 2017/0112744 A1 * | 4/2017 | Tomlinson | A61P 17/16 |
| 2017/0354595 A1 * | 12/2017 | Trimble | A61K 31/522 |
| 2018/0168992 A1 * | 6/2018 | Tokunaga | A61K 8/8158 |

(Continued)

FOREIGN PATENT DOCUMENTS

| | | | | |
|---|---|---|---|---|
| CN | 108113920 A | * | 6/2018 | ............ A61K 8/342 |
| CN | 108 113 920 B | | 3/2021 | |
| EP | 0443741 | | 8/1991 | |

(Continued)

OTHER PUBLICATIONS

Fit Glow Beauty, 10 Reasons Why Silicone is Bad for Your Skin, https://fitglowbeauty.com/blogs/fitglow-blog/10-reasons-why-silicone-is-bad-for-your-skin#:~:text=Silicone%20is%20hard%20to%, Jul. 15, 2019 (Year: 2019).*
Machine Translation of CN108113920A (Year: 2018).*
Machine Translation of EP2221045 (Year: 2010).*
https://www.codageparis.com/en/myscan/index/step0/, Codate Paris, downloaded from the Internet Jun. 13, 2017.
https://www.ricaud.com/en/beauty-advice/facial-care-diagnosis.htm, Pierre Ricaud, downloaded from the Internet Jun. 13, 2017.
International Search Report issued for Application No. PCT/US2018/025111 dated Jun. 22, 2018.
International Search Report issued for Application No. PCT/US2017/025412 dated Jun. 26, 2017.

(Continued)

*Primary Examiner* — Jennifer A Berrios
(74) *Attorney, Agent, or Firm* — McNees Wallace & Nurick LLC

(57) ABSTRACT

A skin care composition includes a gel stabilized emulsion comprising a combination of actives that include azelaic acid, at least one hydroquinone derivative, and niacinamide, at least one anionic polymer thickener, and at least one fatty compound. The provides a hydrating formula that is comfortable for the wearer and is oil free, without appearing shiny or greasy on the skin, and includes actives to treat the appearance of dark spots and inflammatory lesions, including acne, for all skin types. The skin care composition is free or essentially free of monoalcohols, silicones, silicone oils, and oils other than fatty compounds that comprise emollient esters, hydrogenated polyisobutene, and squalane.

18 Claims, No Drawings

(56) References Cited

U.S. PATENT DOCUMENTS

2018/0271760 A1  9/2018  Baca
2019/0151210 A1  5/2019  Dersh et al.

FOREIGN PATENT DOCUMENTS

| EP | 2221045 A1 * | 8/2010 | ........... A61K 8/8147 |
|----|--------------|--------|------------------------|
| WO | 2000064570 | 11/2000 | |
| WO | 2009137277 | 11/2009 | |
| WO | 2010104687 | 9/2010 | |
| WO | 2013113856 | 8/2013 | |
| WO | 2014095204 | 6/2014 | |
| WO | 2015111002 | 7/2015 | |

OTHER PUBLICATIONS

Non-Final Office Action issued by the USPTO for U.S. Appl. No. 15/142,929 dated Feb. 8, 2017.
Final Office Action issued by the USPTO for U.S. Appl. No. 15/142,929 dated May 17, 2017.
Advisory Action issued by the USPTO for U.S. Appl. No. 15/142,929 dated Aug. 23, 2017.
Non-Final Office Action issued by the USPTO for U.S. Appl. No. 15/142,929 dated Nov. 21, 2017.
Final Office Action issued by the USPTO for U.S. Appl. No. 15/142,929 dated Jun. 13, 2018.
Non-Final Office Action issued by the USPTO for U.S. Appl. No. 15/142,929 dated Apr. 1, 2019.
Notice of Allowance issued by the USPTO for U.S. Appl. No. 15/142,929 dated Aug. 2, 2019.
Non-Final Office Action issued by the USPTO for U.S. Appl. No. 15/251,740 dated Nov. 22, 2017.
Final Office Action issued by the USPTO for U.S. Appl. No. 15/251,740 dated May 14, 2018.
Advisory Action issued by the USPTO for U.S. Appl. No. 15/251,740 dated Sep. 27, 2018.
Notice of Allowance issued by the USPTO for U.S. Appl. No. 15/251,740 dated Oct. 23, 2018.
Mintel, "White White Beauties"; XP-002770906; record ID 1584625; http://www.gnpd.com.
Mintel, "Ideal Renewing Ampoule", record ID 4729445, http://www.gnpd.com.
Mintel, "Smooth & Glow Enzyme Mask"; record ID 7631203; http://www.gnpd.com.
Mintel, "Radiant & Bright Glowing Moisturizer"; record ID 7631221; http://www.gnpd.com.
Mintel, "Clear Skin Clarifying Back & Body Spray"; record ID 7044383; http://www.gnpd.com.
Mintel, "Even Tone Smoothing Body Treatment"; record ID 6998541; http://www.gnpd.com.
Mintel, "Dark Spot Rapid Repair Retinol Treatment"; record ID 6397825; http://www.gnpd.com.
Mintel, "Super Glow Serum"; record ID 6397827; http://www.gnpd.com.
Mintel, "Brightening Ampoule"; record ID 4483687; http://www.gnpd.com.
Mintel, "Metamorphosis Softening Serum and Enlightening Lotion"; record ID 1296033; http://www.gnpd.com.
Mintel, "Meso-White Flash Whitening"; record ID 1169900; http://www.gnpd.com.
Mintel, "Sleep & Peel Resurfacing Night Cream"; record ID 818661; http://www.gnpd.com.
US Skincare & Suncare Labs, "Tropicals Faded," iCare ID b50630, Note details of certain ingredient amounts on front of reference.
US Skincare & Suncare Labs, "Sara Elizabeth Arbutin Illuminating Cream," iCare ID B50337, Note details of certain ingredient amounts on front of reference.
US Skincare & Suncare Labs, "OBAGI Nu-Derm Clear FX," iCare ID b49684, NOTE details of certain ingredient amounts on front of reference.
Search Report for counterpart Application No. FR2104188 dated Dec. 10, 2021.
Mintel, Anonymous, Laboratoires Filorga "Meso-White Flash Whitening" Redord ID 1169900, XP002751961, Sep. 1, 2009, www.gnpd.com.
PCT Notification of Transmittal of the International Search Report and the Written Opinion of the International Searching Authority, or the Declaration issued to counterpart Application No. PCT/IB2022/051705 dated May 18, 2022.

* cited by examiner

GEL STABILIZED O/W EMULSION WITH ALPHA-ARBUTIN AND AZELAIC ACID DISPERSION

FIELD OF TECHNOLOGY

The present disclosure is directed to a skin care composition that includes a high level of active ingredients including azelaic acid, hydroquinone derivative, and niacinamide for treating target skin conditions in a pleasing and stable composition.

BACKGROUND

There are a variety of skin conditions that benefit from skin care compositions that may be applied and left on the skin. These conditions include dryness and tightness, dark spots, and inflammatory lesions. A wide variety of leave on skin care products exist for addressing one or more of these types of conditions. Compositions for addressing dryness and tightness often include a high oil content with high amounts of stabilizing thickeners that can cause them to be heavy and leave a greasy skin feel. These compositions may include silicones and silicone oils that can be thinning and adversely affect the pleasant feel associated with a creamy hydrating formulation. Further, to assist in solvating and stabilizing actives for lightening and brightening, alcohols and silicones are often used, which can be drying and irritating to skin. These limitations present challenges to providing a stable composition that offers light weight moisturizing with sufficient amounts of actives to ameliorate inflammation, hyperpigmentation and acne.

Accordingly, there is a need for a composition that overcomes the shortcomings of the prior art and provides benefits that include delivery of hydration and high actives to address pigmentation and acne issues, in a creamy, light formulation that is creamy upon initial application to skin and breaks into a watery gel upon rubbing and does not leave the skin oily. The present invention provides such a composition.

BRIEF SUMMARY

In an exemplary embodiment, the invention provides a skin care composition that includes a high level of active ingredients including azelaic acid, at least one hydroquinone derivative, and niacinamide and at least one anionic polymer thickener to provide a temperature-stable gel stabilized emulsion type architecture that upon initial application to a keratinous tissue breaks into a watery gel upon rubbing.

In the various embodiments, the combination of the active ingredients that include the azelaic acid, the at least one hydroquinone derivative, and the niacinamide are present together as a combination (the "active ingredient combination").

In various embodiments, the skin care composition also includes an "oily" phase components that include squalane, and one or more other fatty compounds that comprise emollient esters, for example, isononyl isononanoate, hydrogenated polyisobutene, or combinations of these.

In various embodiments, the skin care composition also includes in the water phase or the oily phase additional components that include one or more water-soluble solvents, humectants, other actives, preservatives, pH adjusters, chelating agents, dyes, pigments, fragrance, or any combinations of these.

The skin care composition is free or essentially free of monoalcohols, silicones, silicone oils, and oils other than fatty compounds that comprise emollient esters, hydrogenated polyisobutene, and squalane.

Thus, in various embodiments, the skin care composition comprises a gel stabilized emulsion comprising:
  i. an active ingredient combination comprising a combination of actives that include azelaic acid present in a range from about 0.5% to about 5%, at least one hydroquinone derivative present in a range from about 0.5% to about 5%, and niacinamide present in a range from about 0.5% to about 4.0%, all based on the total weight of the skin care composition;
  ii. at least one anionic polymer thickener; and
  iii. at least one fatty compound.

In some embodiments azelaic acid is present in a range from about 0.5% to about 4.5%, based on the total weight of the skin care composition. In some embodiments azelaic acid is present in a range from about 0.5% to about 3.5%. In some embodiments azelaic acid is present in a range from about 0.5% to about 3.0%. In some embodiments azelaic acid is present in a range from about 1% to about 3.5%. In some embodiments azelaic acid is present in a range from about 2.5% to about 3.5%.

In some embodiments the at least one hydroquinone derivative is present in a range from about 0.5% to about 4.5%, based on the total weight of the skin care composition. In some embodiments hydroquinone derivative is present in a range from about 0.5% to about 4.0%. In some embodiments hydroquinone derivative is present in a range from about 0.5% to about 3.0%. In some embodiments hydroquinone derivative is present in a range from about 1% to about 3.0%. In some embodiments hydroquinone derivative is present in a range from about 1.5% to about 2.5%.

In some embodiments the at least one hydroquinone derivative is alpha arbutin.

In some embodiments niacinamide is present in a range from about 0.5% to about 3.5%, based on the total weight of the skin care composition. In some embodiments niacinamide is present in a range from about 0.5% to about 3.0%. In some embodiments niacinamide is present in a range from about 1% to about 3.5%. In some embodiments niacinamide is present in a range from about 0.5% to about 2.5%. In some embodiments niacinamide is present in a range from about 2.0% to about 3.0%.

In some embodiments the at least one anionic polymer is present in a range from about 0.05% to about 3%, based on the total weight of the skin care composition. In some embodiments, each of the at least one anionic polymer is present in a range from about 0.05% to about 3%. In some embodiments, the total amount of anionic polymer is present in a range from about 0.05% to about 3%.

In some embodiments the at least one anionic polymer comprises one or more of ammonium polyacryloyldimethyl taurate, hydroxyethyl acrylate/sodium acryloyldimethyl taurate copolymer, or a combination thereof. In some embodiments the at least one anionic polymer comprises both ammonium polyacryloyldimethyl taurate, and hydroxyethyl acrylate/sodium acryloyldimethyl taurate copolymer.

In some embodiments the at least one fatty compound is present in a range from about 1% to about 15%, based on the total weight of the skin care composition. In some embodiments, each of the at least one fatty compound is present in a range from about 1% to about 15%. In some embodiments, the total amount of fatty compound is present in a range from about 1% to about 15%.

In some embodiments the at least one fatty compound comprises one or more of hydrogenated polyisobutene, isononyl isononanoate, squalane, or a combination thereof.

In some embodiments the at least one fatty compound comprises each of hydrogenated polyisobutene, isononyl isononanoate, and squalane.

In some embodiments, the skin care composition comprises a gel stabilized emulsion comprising a combination of actives that include azelaic acid, at least one hydroquinone derivative, and niacinamide; at least one anionic polymer thickener; and at least one fatty compound, wherein:
 i. in the combination of actives that include azelaic acid, at least one hydroquinone derivative, and niacinamide,
   a. azelaic acid is present in a range from about 0.5% to about 5%;
   b. the at least one hydroquinone derivative is present in a range from about 0.5% to about 5%; and
   c. niacinamide is present in a range from about 0.5% to about 4%;
 ii. the at least one anionic polymer is present in a range from about 0.05% to about 3%; and
 iii. the at least one fatty compound is present in a range from about 1% to about 15%, all amounts by weight based on the total weight of the skin care composition.

In some embodiments, the skin care composition comprises a gel stabilized emulsion comprising a combination of actives that include azelaic acid present in a range from about 0.5% to about 5%, at least one hydroquinone derivative present in a range from about 0.5% to about 5%, and niacinamide present in a range from about 0.5% to about 4.0%, all amounts by weight, based on the total weight of the skin care composition; at least one anionic polymer thickener; and at least one fatty compound, wherein:
 i. in the combination of actives that include azelaic acid, at least one hydroquinone derivative, and niacinamide, the at least one hydroquinone derivative is alpha arbutin;
 ii. the at least one anionic polymer comprises ammonium polyacryloyldimethyl taurate and hydroxyethyl acrylate/sodium acryloyldimethyl taurate copolymer; and
 iii. the at least one fatty compound comprises hydrogenated polyisobutene, isononyl isononanoate, and squalane.

The invention also provides a method for forming a skin care composition comprising a combination of actives that include azelaic acid, at least one hydroquinone derivative, and niacinamide; at least one anionic polymer thickener; and at least one fatty compound, the method comprising: providing the at least one hydroquinone derivative and niacinamide solubilized in a water phase; blending azelaic acid with the water phase; combining an oil phase with the water phase to provide an emulsion.

Other features and advantages of the present disclosure will be apparent from the following more detailed description of the preferred embodiment which illustrates, by way of example, the principles of the disclosure.

DETAILED DESCRIPTION

The term "cosmetically acceptable" means a carrier that is compatible with any keratinous substrate.

The term "emulsion architecture" means that the skin care composition has the properties generally associated with an oil in water emulsion.

The terms "keratinous substrate" and "keratinous tissue" each includes but is not limited to skin, hair, and nails.

The term "skin" means and includes skin materials containing keratin such as facial and body skin, scalp, eyebrows, and lips.

The invention provides a skin care composition that includes a high level of active ingredients including azelaic acid, at least one hydroquinone derivative, and niacinamide and at least one anionic polymer thickener to provide a temperature-stable gel stabilized emulsion type architecture that is creamy upon initial application to a keratinous tissue and breaks into a watery gel upon rubbing.

The skin care composition when applied provides the sensorial effect of creamy initial application that breaks into a watery gel upon rubbing. This provides the user with a sense of hydration without a heavy oily feeling and is well suited for users with oily skin or those that prefer a lightweight moisturizer. The skin care composition is an emulsion with a water phase containing the actives and any "oily-type" phase that excludes typical oils and silicone oils often found in similar types of skin care formulations. In a representative embodiment according to the disclosure, the "oil" phase includes of isononyl isononanoate and squalane, and anionic polymer thickeners that include ammonium polyacryloyldimethyl taurate and hydroxyethyl acrylate/sodium acryloyldimethyl taurate copolymer, present in a total amount of about 0.05% to about 3% and in some such embodiments, these are present at about 1.5%. Without being bound by theory, it is posited that the anionic polymer thickeners stabilize the emulsion by stabilizing the isononyl isononanoate and squalane and likewise stabilizing the azelaic acid dispersion, particularly when the azelaic acid is present in a high amount, for example, at about 3%, together with about 2.5% niacinamide and about 2% alpha-arbutin, all by weight, based on the weight of the skin care composition.

In some representative embodiments, the skin care composition also includes other active ingredients that include a blend of botanicals, such as cucumber extract, and olive leaf extract, as well as about 5% glycerin, about 3% propylene glycol, and silica silylate to produce a mattifying finish. The skin care composition is optimal for users with acne-prone skin, post-inflammatory hyperpigmentation, post-inflammatory erythema, oily skin, and skin in need of hydration.

The skin care composition demonstrates surprising benefits wherein the inventive skin care composition comprises relatively high amounts of the actives, particularly in the combination of actives that include azelaic acid, at least one hydroquinone derivative, and niacinamide, and remains stable without separation of the actives over a wide temperature range for at least two months/8 weeks. In some embodiments, the skin care composition may be especially hydrating and comfortable for the wearer and is oil free, without appearing shiny or greasy on the skin, and includes actives to treat the appearance of dark spots and inflammatory lesions, including acne, for all skin types.

The terms "stable" and "stability" with respect to the emulsion architecture of the skin care composition refers to the skin care composition remaining in a creamy emulsion state and not phase separating as evidenced by the formation of significant fluid droplets. In some embodiments, stable or stability may include the absence of or minimal formation of crystals. Such properties may be achieved even with the inclusion of high amounts of actives and in the absence of silicones and silicone oils. Stability is evidenced by one or both of direct measurement of viscosity, pH stability, and microscopic inspection, and by visual inspection. In various embodiments, an inventive composition remains stable at temperatures in the range from about 5° C. to about 45° C., over a time period of at least two months, and may remain stable for longer, for example for at least three months, or at least four months, or at least six months, and up to about at least 3 years, or any value, range, or sub-range therebetween. The exemplified inventive skin care compositions shown in the examples herein demonstrated stability at each of 5° C., 25° C., 37° C., and 45° C. for a period of eight weeks. And such exemplified compositions demonstrated stability for 10 freeze-thaw cycles at −20° C./25° C.

In the various embodiments, the skin care composition is free or essentially free of monoalcohols, silicones, silicone oils, and oils other than fatty compounds that comprise emollient esters, hydrogenated polyisobutene, and squalane. Thus, in the various embodiments, as otherwise disclosed herein, the skin care composition may comprise one or more of fatty compounds that comprise emollient esters, hydrogenated polyisobutene, and squalane.

For purposes hereof, free of or essentially free of "excluded components" that include monoalcohols, silicones, silicone oils, and oils other than fatty compounds that comprise emollient esters, hydrogenated polyisobutene, and squalane means that any excluded agent is absent or if present, is present in an amount that is at or below 1%, or 0.5%, or 0.1% of such excluded agent, based on the total weight of the skin care composition. In some embodiments, the skin care composition is devoid of any or all of the excluded agents.

In the various embodiments, the skin care composition is free or essentially free of monoalcohols, for example, but not limited to, monohydric $C_1$-$C_8$ alcohols selected from the group consisting of ethanol, propanol, butanol, isopropanol, isobutanol, and benzyl alcohol, and phenylethyl alcohol.

In the various embodiments, the skin care composition is free or essentially free of silicones. In particular, in the various embodiments, the skin care composition is free or essentially free of silicone oils, for example, silicone oils selected from, but not limited to, the group consisting of dimethicone, dimethiconol, silicone crosspolymers, silicone copolymers, and polysiloxanes.

Skin Care Composition Ingredients

As further described herein, the skin care composition includes, in various embodiments, a combination of the active ingredients that include azelaic acid, at least one hydroquinone derivative, and niacinamide, present together as a combination of active ingredients (the "active ingredient combination"), with at least one anionic polymer thickener. As shown in the exemplified embodiments of the skin care composition herein, the active ingredient combination relative to the total amount of anionic polymer thicker is present in a ratio of about 4.5:1 wherein there is about 7.5% of the active ingredient combination and about 1.6% of the anionic polymer thicker, all weights based on the total weight of the skin care composition.

In various embodiments, the skin care composition also includes an "oily" phase components that include squalane, and one or more other fatty compounds that comprise emollient esters, for example, isononyl isononanoate, hydrogenated polyisobutene, or combinations of these. And the skin care composition also includes in the water phase additional components that include one or more water-soluble solvents, humectants, other actives, preservatives, pH adjusters, chelating agents, pigments, fragrance, or any combinations of these, together with water and the at least one hydroquinone derivative, and the niacinamide.

The skin care composition is free or essentially free of monoalcohols, silicones, silicone oils, and oils other than fatty compounds that comprise emollient esters, hydrogenated polyisobutene, and squalane.

Azelaic Acid, Hydroquinone Derivative, and Niacinamide

The skin care composition includes an active ingredient combination comprising azelaic acid, at least one hydroquinone derivative, and niacinamide. In some particular embodiments, the hydroquinone derivative is alpha arbutin.

Azelaic Acid

In the various embodiments, the azelaic acid is present in the skin care composition in a range from about 0.5% to about 5% by weight, based on the weight of the skin care composition, or from about 0.5% to about 4.5%, or from about 0.5% to about 3.5%, or from about 0.5% to about 3.0%, or from about 1% to about 3.5%, or from about 1.0% to about 3.5%, or from about 2.5% to about 3.5%, or from about 0.75% to about 1%, or from about 0.5% to about 2.5%, or from about 0.5% to about 0.75%, or any suitable combination, sub-combination, range, or sub-range thereof by weight, based on the weight of the skin care composition. One of ordinary skill in the art, however, will appreciate that other ranges are within the scope of the invention.

Thus, the azelaic acid is present in the skin care composition, by weight, based on the total weight of the skin care composition, from about 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9 to about 5.0 percent, including increments and ranges therein and there between.

Hydroquinone Derivative

In the various embodiments, the at least one hydroquinone derivative is present in the skin care composition in a range from about 0.5% to about 5% by weight, based on the weight of the skin care composition, or from about 0.5% to about 4.5%, or from about 0.5% to about 4.0%, or from about 0.5% to about 3.0%, or from about 1% to about 3.0%, or from about 1.5% to about 2.5%, or from about 1.0% to about 3.5%, or from about 1.0% to about 3.0%, or from about 2.5% to about 3.5%, or from about 0.75% to about 1%, or from about 0.5% to about 2.5%, or from about 0.5% to about 0.75%, or any suitable combination, sub-combination, range, or sub-range thereof by weight, based on the weight of the skin care composition. One of ordinary skill in the art, however, will appreciate that other ranges are within the scope of the invention.

Thus, the at least one hydroquinone derivative is present in the skin care composition, by weight, based on the total weight of the skin care composition, from about 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9 to about 5.0 percent, including increments and ranges therein and there between.

Niacinamide

In the various embodiments, niacinamide is present in the skin care composition in a range from about 0.5% to about 4% by weight, based on the weight of the skin care composition, or from about 0.5% to about 3.5%, or from about 0.5% to about 3.0%, or from about 1% to about 3.5%, or from about 0.5% to about 2.5%, or from about 2.0% to about 3.0%, or from about 2.5% to about 3.5%, or from about 0.75% to about 1%, or from about 0.5% to about 2.5%, or from about 0.5% to about 0.75%, or any suitable combination, sub-combination, range, or sub-range thereof by weight, based on the weight of the skin care composition. One of ordinary skill in the art, however, will appreciate that other ranges are within the scope of the invention.

Thus, niacinamide is present in the skin care composition, by weight, based on the total weight of the skin care composition, from about 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, to about 4.0 percent, including increments and ranges therein and there between.

Thickener

In accordance with the disclosure, the skin care composition includes at least one anionic polymer thickener. The at least one anionic polymer thickener may be selected from, for example, ammonium polyacryloyldimethyl taurate copolymer, hydroxyethyl acrylate/sodium acryloyldimethyl taurate copolymer, or a combination thereof. In some embodiments, the skin care composition includes at least two anionic polymer thickeners. Other examples of suitable anionic polymer thickeners includes at least one of a thickener selected from xanthan gum, cellulose gum, acrylate crosspolymers, acrylate copolymers, sodium polyacrylate, poly acrylate cross polymers, or a combination thereof.

In accordance with the various embodiments, each anionic polymer thickener is present in the skin care composition in an amount from about 0.05% to about 3%, or from about 0.075% to about 1%, or from about 0.5% to about 2.5%, or from about 0.5% to about 0.75%, or from about 0.1% to about 0.2%, or from about 1% to about 1.5%, or any suitable combination, sub-combination, range, or sub-range thereof by weight, based on the weight of the skin care composition. And in some embodiments, the total amount of thickener present in the skin care composition in an amount from about 0.05% to about 3%, or any suitable combination, sub-combination, range, or sub-range thereof by weight, based on the weight of the skin care composition. One of ordinary skill in the art, however, will appreciate that other ranges are within the scope of the invention.

In some embodiments, the skin care composition includes at least two anionic polymer thickeners, comprising, for example, each of ammonium polyacryloyldimethyl taurate copolymer and hydroxyethyl acrylate/sodium acryloyldimethyl taurate copolymer, each present in a range from about 0.05% to about 3%, or as combined in a range from about 0.05% to about 3%, and in some particular embodiments the total amount is about 1.5% to about 1.75%.

Thus, the at least one anionic polymer thickener is present by weight, based on the total weight of the skin care composition, from about 0.05, 0.06, 0.07, 0.08, 0.09, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, to about 3.0 percent, including increments and ranges therein and there between.

Fatty Compounds

In accordance with the disclosure, the skin care composition includes at least one fatty compound selected from emollient esters, hydrogenated polyisobutene, and squalane. In some embodiments, the skin care composition comprises more than one fatty compound. In some particular embodiments, the skin care composition includes a combination of fatty compounds comprising hydrogenated polyisobutene, isononyl isononanoate, and squalane.

In some embodiments, the at least one fatty compound is an emollient ester, that has a carbon chain length of C12 to C24. In some embodiments, the at least one emollient ester is an alkylated alcohol ester. In some embodiments, the at least one emollient ester has a formula RCOOR' in which R represents a linear or branched fatty acid residue containing from 1 to 40 carbon atoms and R' represents a hydrocarbon-based chain that is especially branched, containing from 1 to 40 carbon atoms on condition that R+R' is ȳ 10, for instance Purcellin oil (cetearyl octanoate), isopropyl myristate, isopropyl palmitate, C12-C15 alkyl benzoate, such as the product sold under the trade name Finsolv TN® or Witconol TN® by Witco or Tegosoft TN® by Evonik Goldschmidt, 2-ethylphenyl benzoate, such as the commercial product sold under the name X-Tend 226 by ISP, isopropyl lanolate, hexyl laurate, diisopropyl adipate, isononyl isononanoate, oleyl erucate, 2-ethylhexyl palmitate, isostearyl isostearate, diisopropyl sebacate, such as the product sold under the name of "Dub Dis" by Stearinerie Dubois, octanoates, decanoates or ricinoleates of alcohols or polyalcohols, such as propylene glycol dioctanoate; hydroxylated esters, such as isostearyl lactate or diisostearyl malate; and pentaerythritol esters; citrates or tartrates, such as di(linear C12-C13 alkyl) tartrates, such as those sold under the name Cosmacol ETI® by Enichem Augusta Industriale, and also di(linear C14-C15 alkyl) tartrates, such as those sold under the name Cosmacol ETL® by the same company; or acetates In various embodiments, the at least one fatty compound is present from about 1% to about 15% by weight of the skin care composition, and in some embodiments, from about 1% to about 10%, and in some embodiments, from about 1% to about 7%, and in some embodiments, from about 2% to about 5%, and in some embodiments, about 5% or about 2%, or any suitable combination, sub-combination, range, or sub-range thereof by weight, based on the weight of the skin care composition. In some embodiments, the skin care composition comprises more than one fatty compound, the combination thereof present in the skin care composition at a concentration, from about 1% to about 20%, and each of the more than one present in the skin care composition at a concentration from about 1% to about 15%, or any suitable combination, sub-combination, range, or sub-range thereof by weight, based on the weight of the skin care composition. One of ordinary skill in the art, however, will appreciate that other ranges are within the scope of the invention.

Thus, in various embodiments, each one or a combination of the at least one fatty compound is present in a composition according to the disclosure from about 1, 2, 3, 4, 5, 6, 7, 8, 9, 10, 11, 12, 13, 14, to about 15 percent, by weight, including increments and ranges therein and there between.

Water

In accordance with the disclosure, the skin care composition includes water, by weight, in an amount from about 20% to about 90%, or about 30% to about 80%, or about 40% to about 70%, or any value, range, or sub-range therebetween. One of ordinary skill in the art, however, will appreciate that other ranges are within the scope of the invention.

Thus, any water is present, by weight, based on the total weight of the skin care composition, from about 20, 21, 22, 23, 23, 25, 26, 27, 28, 29, 30, 31, 32, 33, 34, 35, 36, 37, 38, 39, 40, 41, 42, 43, 44, 45, 46, 47, 48, 49, 50, to about 50 weight percent, including increments and ranges therein and there between.

Water-Soluble Solvents

In accordance with some embodiments, the skin care composition may include one or more water-soluble solvent. The term "water-soluble solvent" is interchangeable with the term "water-miscible solvent" and means a compound that is liquid at 25° C. and at atmospheric pressure (760 mmHg), and it has a solubility of at least 50% in water under these conditions. In some cases, the water-soluble solvent has a solubility of at least 60%, 70%, 80%, or 90% in water under these conditions. Non-limiting examples of water-soluble solvents include, for example, glycerin, alcohols (for example, C1-C30, C1-C15, C1-C10, or C1-C4 alcohols), polyols, glycols, and combinations thereof.

Examples of water-soluble solvents, ethylene glycol, propylene glycol, butylene glycol, hexylene glycol, propane diol, and glycerin. The organic solvents can be volatile or non-volatile compounds. Further non-limiting examples of water-soluble solvents include alkanols (polyhydric alcohols such as glycols and polyols) such as glycerin, 1,2,6-hexanetriol, trimethylolpropane, ethylene glycol, propylene glycol, diethylene glycol, butylene glycol, hexylene glycol, triethylene glycol, tetraethylene glycol, pentaethylene glycol, dipropylene glycol, 1,3-butanediol, 2,3-butanediol, 1,4-butanediol, 3-methyl-1,3-butanediol, 1,5-pentanediol, tetraethylene glycol, 1,6-hexanediol, 2-methyl-2,4-pentanediol, polyethylene glycol, 1,2,4-butanetriol, 1,2,6-hexanetriol, 2-butene-1,4-diol, 2-ethyl-1,3-hexanediol, 2-methyl-2,4-pentanediol, (caprylyl glycol), 1,2-hexanediol, 1,2-pentanediol, and 4-methyl-1,2-pentanediol; alkyl alcohols having 1 to 4 carbon atoms such as ethanol, methanol, butanol, propanol, and isopropanol; glycol ethers such as ethylene glycol monomethyl ether, ethylene glycol monoethyl ether, ethylene glycol monobutyl ether, ethylene glycol monomethyl ether acetate, diethylene glycol monomethyl ether, diethylene glycol monoethyl ether, diethylene glycol mono-n-propyl ether, ethylene glycol mono-iso-propyl ether, diethylene glycol mono-iso-propyl ether, ethylene glycol mono-n-butyl ether, ethylene glycol mono-t-butyl ether, diethylene glycol mono-t-butyl ether, 1-methyl-1-methoxybutanol, propylene glycol monomethyl ether, propylene glycol monoethyl ether, propylene glycol mono-t-butyl ether, propylene glycol mono-n-propyl ether, propylene glycol mono-iso-propyl ether, dipropylene glycol monomethyl ether, dipropylene glycol monoethyl ether, dipropylene glycol mono-n-propyl ether, and dipropylene glycol mono-iso-propyl ether; 2-pyrrolidone, N-methyl-2-pyrrolidone, 1,3-dimethyl-2-imidazolidinone, formamide, acetamide, dimethyl sulfoxide, sorbit, sorbitan, acetine, diacetine, triacetine, sulfolane, and combinations thereof.

In accordance with the various embodiments, the total amount of the water-soluble solvent, when present, is present from about 0.5% to about 25%, or from about 0.5% to about 20%, or from about 1% to about 20%, or from about 1% to about 10%, or from about 2% to about 5% or any suitable combination, sub-combination, range, or sub-range thereof by weight, based on the weight of the skin care composition. One of ordinary skill in the art, however, will appreciate that other ranges are within the scope of the invention.

Thus, any one water-soluble solvent, when present, is present, by weight, based on the total weight of the skin care composition, from about 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24 to about 25 weight percent, including increments and ranges therein and there between.

It will be appreciated by a skilled artisan that any non-water solvents are present only to the extent and in amounts that do not materially adversely affect the basic and novel characteristic(s) of the claimed disclosure.

Humectant/Hydrating Agent

In accordance with the disclosure, one or more humectants may be present in the skin care composition. In some embodiments, the humectant may comprise one or more of polyols, including, for example, glycerin, glycerol, glycols, such as, caprylyl glycol, butylene glycol, propylene glycol, isoprene glycol, dipropylene glycol, hexylene glycol and polyethylene glycols, monoethylene glycol, diethylene glycol, triethylene glycol, diethylene glycol, hexylene glycol, glycol ethers, such as, monopropylene, dipropylene and tripropylene glycol alkyl(C1-C4)ethers, squalane, triacetin, sugars, such as, glucose, xylitol, maltitol, sorbitol, sucrose pentaerythritol, inositol, pyrrolidone carboxylic acid, lactic acid, lithium chloride, acetamide MEA, sodium lactate, urea, dicyanamide, hyaluronic acid, aloe vera, honey, and seaweed extract.

In accordance with the various embodiments, the amount of humectant present in the skin care composition can range from about 1% to about 10%, or from about 1% to about 8%, or from about 1% to about 5%, or from about 2% to about 3%, or any suitable combination, sub-combination, range, or sub-range thereof by weight, based on the weight of the skin care composition. One of ordinary skill in the art, however, will appreciate that other ranges are within the scope of the invention.

Thus, any one of or a combination of humectant, when present, may be present, by weight, based on the total weight of the skin care composition, is from about 1, 2, 3, 4, 5, 6, 7, 8, 9, to about 10 weight percent, including increments and ranges therein and there between.

It will be appreciated by a skilled artisan that any humectants are present only to the extent and in amounts that do not materially adversely affect the basic and novel characteristic(s) of the claimed disclosure.

Preservatives

In accordance with the disclosure, one or more preservatives and/or antimicrobials may be present in the skin care composition. Any preservative commonly used in cosmetic skin care compositions is an acceptable preservative for the skin care compositions herein, such as phenoxyethanol, members from the paraben family such as the methyl, ethyl, propyl, butyl or isobutyl parabens, 4-hydroxy benzoic acid, benzoic acid, sorbic acid, dehydroacetic acid, triclosan, benzyl alcohol, chlorophenesin, or salicylic acid, for example. At more concentrated amounts of suitable solvents for optional additives, in particular, suitable solvents for antimicrobials and preservatives, members from the paraben family may be used as a preservative.

In some embodiments, the preservative may comprise one or more of preservatives selected from the group consisting of organic acids, parabens, formaldehyde donors, phenol derivatives, quaternary ammoniums, alcohols, isothiazolinones, and combinations thereof. Preservatives having antibacterial activity are optionally present in the skin care compositions of the present invention. Examples of organic acid preservatives include, but are not limited to, sodium benzoate, potassium sorbate, benzoic acid and dehydroacetic acid, sorbic acid, and combinations thereof. A preferred organic acid preservative system includes a mixture of sodium benzoate and potassium sorbate. Examples of paraben preservatives include, but are not limited to, alkyl para-hydroxybenzoates, wherein the alkyl radical has from 1, 2, 3, 4, 5 or 6 carbon atoms and for example, from 1 to 4 carbon atoms e.g., methyl para-hydroxybenzoate (methylparaben), ethyl para-hydroxybenzoate (ethylparaben), propyl para-hydroxybenzoate (propylparaben), butyl para-hydroxybenzoate (butylparaben) and isobutyl para-hydroxybenzoate (isobutylparaben). Examples of formaldehyde donor preservatives include, but are not limited to, 1,3-Dimethylol-5,5-dimethylhydantoin (DMDM hydantoin), imidazolidinyl urea, gluteraldehyde, and combinations thereof. Examples of quaternary ammonium preservatives include, but are not limited to, benzalkonium chloride, methene ammonium chloride, benzethonium chloride, and combinations thereof. Examples of alcohol preservatives include, but are not limited to, ethanol, benzyl alcohol, dichlorobenzyl alcohol, phenoxyethanol, and combinations thereof. Examples of isothiazolone preservatives include, but are not limited to, methylchloroisothiazolinone, methylisothiazolinone, and combinations thereof.

In some embodiments, the preservative includes one or more preservatives, the one or combination present at a concentration, by weight of about 0.001% to about 5%, or alternatively about 0.05% to about 2.5% or alternatively about 0.1% to about 2.0%, based upon weight of the skin care composition. One of ordinary skill in the art, however, will appreciate that other ranges are within the scope of the invention.

Thus, any one of or a combination of preservatives, when present, may be present, by weight, based on the total weight of the skin care composition, is from about 0.001, 0.002, 0.003, 0.004, 0.005, 0.006, 0.007, 0.008, 0.009, 0.01, 0.02, 0.03, 0.04, 0.05, 0.06, 0.07, 0.08, 0.09, 1.0, 1.1, 1.2, 1.3, 1.4, 1.5, 1.6, 1.7, 1.8, 1.9, 2, 3, 4, to about 5 weight percent, including increments and ranges therein and there between.

It will be appreciated by a skilled artisan that any preservatives are present only to the extent and in amounts that do not materially adversely affect the basic and novel characteristic(s) of the claimed disclosure.

Optional Additives

In some embodiments, a skin care composition includes at least one additive used in the cosmetics field which does not affect the properties of the skin care composition according to the invention, such as, other actives, for example, sodium hyaluronate or hyaluronic acid, hydroxyacetophenone and other antioxidants, fragrances, chelating agents, pH adjusters (citric acid, sodium chloride; neutralizing or pH-adjusting agents (e.g., triethylamine (TEA) and sodium hydroxide), and combinations thereof), other cosmetically acceptable additives, such as but not limited to, pearlescent agents, silica silylate, dyes, and coloring materials; essential oils; fruit extracts, for example, *Cucumis sativus* fruit extract, *Rosmarinus Officinalis* leaf extract, *Citrus Grandis* fruit extract, *Thymus Vulgaris* flower/leaf extract, *Morus Alba* root extract, *Olea Europaea* leaf extract, *Pyrus* Malus (Apple) Fruit Extract, and Aloe Barbadensis Leaf Juice Powder. Although the optional additives are given as examples, it will be appreciated that other optional components compatible with cosmetic applications known in the art may be used.

In accordance with the various embodiments, the amount of one or more additives, alone or in combination, present in the skin care composition can be present in the skin care composition according to the disclosure in a range from about 0.001% to about 20%, by weight, or from about 0.005% to about 0.01%, or from about 0.01% to about 0.1%, or from about 0.15% to about 5%, or from about 0.40% to about 4%, or from about 0.5% to about 2.5% by weight, or from about 1% to about 2%, or any suitable combination, sub-combination, range, or sub-range thereof by weight, based on the total weight of the skin care composition. One of ordinary skill in the art, however, will appreciate that other ranges are within the scope of the invention.

Thus, any one or a combination of additives may be present, by weight, based on the total weight of the skin care composition, each one or the combination present from about 0.001, 0.002, 0.003, 0.004, 0.005, 0.006, 0.007, 0.008, 0.009, 0.01, 0.02, 0.03, 0.04, 0.05, 0.06, 0.07, 0.08, 0.09, 0.10, 0.20, 0.30, 0.40, 0.50, 0.60, 0.70, 0.80, 0.90, 1.0, 2, 3, 4, 5, 6, 7, 8, 9, 10, 11, 12, 13, 14, 15, 16, 17, 18, 19 to about 20 weight percent, including increments and ranges therein and there between.

Although the optional additives are given as examples, it will be appreciated that other optional components compatible with cosmetic applications known in the art may be used that are suitable. It will be appreciated by a skilled artisan that any optional additives are present only to the extent and in amounts that do not materially adversely affect the basic and novel characteristic(s) of the claimed disclosure.

EXAMPLES

The following examples are intended to further illustrate the present disclosure. They are not intended to limit the disclosure in any way. Unless otherwise indicated, all parts are by weight.

TABLE 1 lists the ingredients of two embodiments of the Inventive skin care composition.

TABLE 1

| INGREDIENT | Exemplary Inventive Amounts/Ranges |
| --- | --- |
| AZELAIC ACID | ~3% |
| ALPHA-ARBUTIN | ~2% |
| NIACINAMIDE | ~2.5% |
| HYDROXYETHYL ACRYLATE/SODIUM ACRYLOYLDIMETHYL TAURATE COPOLYMER, and AMMONIUM POLYACRYLOYLDIMETHYL TAURATE | ~1.6% |
| HYDROGENATED POLYISOBUTENE | ~0.8%-1% |
| SQUALANE | ~1.5%-2% |
| ISONONYL ISONONANOATE | ~3.5%-4% |
| SILICA SILYLATE | ~0.2% to about 0.6% |
| HYDROXYACETOPHENONE, SODIUM HYALURONATE, CUCUMIS SATIVUS FRUIT EXTRACT, ROSMARINUS OFFICINALIS LEAF EXTRACT, PROPYLENE GLYCOL (and) CITRUS GRANDIS FRUIT EXTRACT, GLYCERIN (and) THYMUS VULGARIS FLOWER/LEAF EXTRACT, MORUS ALBA ROOT EXTRACT, OLEA EUROPAEA LEAF EXTRACT | Each ~ 0.1%-3%; total ~06.5% |
| GLYCERIN and/or PROPYLENE GLYCOL | ~3%-5% of one or both |
| SODIUM HYDROXIDE, PARFUM, DYES | ~0.0002% to about 0.1% each |
| CAPRYLYL GLYCOL | ~0.1%-0.2% |
| AQUA | ~65%-75% |

In one representative embodiment, the skin care composition includes about 3% azelaic acid, together with about 2.5% niacinamide and about 2% alpha-arbutin, anionic polymer that includes both ammonium polyacryloyldimethyl taurate, and hydroxyethyl acrylate/sodium acryloyldimethyl taurate copolymer present in a total amount of about 1.6% the ammonium polyacryloyldimethyl taurate present in a range from about 0.05% to about 0.2% and the hydroxyethyl acrylate/sodium acryloyldimethyl taurate copolymer present from about 1.2% to about 1.5%, at least one fatty compound including polyisobutene present from about 0.8% to about 1%, isononyl isononanoate present from about 3.5% to about 4%, squalane present from about 1.5% to about 2%, all by weight based on the weight of the skin care composition, and also including other active ingredients that include hydroxyacetophenone, sodium hyaluronate, a blend of botanicals, such as cucumber extract, and olive leaf extract, as well as about 5% glycerin and/or about 3% propylene glycol, and about 0.2% to about 0.6% silica, and optionally antimicrobial/preservative, pH adjusters, perfumes and dyes.

Example 2. Demonstration of Stability of Inventive Compositions

Compositions according to the formulae shown in Example 1 were evaluated for stability. Each of the inventive compositions demonstrated stability including no phase separation.

While the disclosure has been described with reference to a preferred embodiment, it will be understood by those skilled in the art that various changes may be made and equivalents may be substituted for elements thereof without departing from the scope of the disclosure. In addition, many modifications may be made to adapt a particular situation or material to the teachings of the disclosure without departing from the essential scope thereof. While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

The articles "a" and "an," as used herein, mean one or more when applied to any feature in embodiments of the present disclosure described in the specification and claims. The use of "a" and "an" does not limit the meaning to a single feature unless such a limit is specifically stated. The article "the" preceding singular or plural nouns or noun phrases denotes a particular specified feature or particular specified features and may have a singular or plural connotation depending upon the context in which it is used. The adjective "any" means one, some, or all indiscriminately of whatever quantity.

"At least one," as used herein, means one or more and thus includes individual components as well as mixtures/combinations.

The transitional terms "comprising," "consisting essentially of" and "consisting of," when used in the appended claims, in original and amended form, define the claim scope with respect to what unrecited additional claim elements or steps, if any, are excluded from the scope of the claim(s). The term "comprising" is intended to be inclusive or open-ended and does not exclude any additional, unrecited element, method, step or material. The term "consisting of" excludes any element, step or material other than those specified in the claim and, in the latter instance, impurities ordinarily associated with the specified material(s). The term "consisting essentially of" limits the scope of a claim to the specified elements, steps or material(s) and those that do not materially affect the basic and novel characteristic(s) of the claimed disclosure. All materials and methods described herein that embody the present disclosure can, in alternate embodiments, be more specifically defined by any of the transitional terms "comprising," "consisting essentially of," and "consisting of."

The terms "free" and "devoid" indicates that no reliably measurable excluded material is present in the skin care composition, typically 0% by weight, based on the total weight of the skin care composition. The term "essentially free" means that, while it prefers that no excluded material is present in the skin care composition, it is possible to have very small amounts of the excluded material in the skin care composition of the invention, provided that these amounts do not materially affect the advantageous properties of the skin care composition. In particular, "essentially free" means that excluded material can be present in the skin care composition at an amount of less than about 0.1% by weight, based on the total weight of the skin care composition.

All percentages and ratios are calculated by weight unless otherwise indicated. All percentages are calculated based on the total composition unless otherwise indicated. Generally, unless otherwise expressly stated herein, "weight" or "amount" as used herein with respect to the percent amount of an ingredient refers to the amount of the raw material comprising the ingredient, wherein the raw material may be described herein to comprise less than and up to 100% activity of the ingredient. Therefore, weight percent of an active in a composition is represented as the amount of raw material containing the active that is used and may or may not reflect the final percentage of the active, wherein the final percentage of the active is dependent on the weight percent of active in the raw material.

All ranges and amounts given herein are intended to include subranges and amounts using any disclosed point as an end point. Thus, a range of "1% to 10%, such as 2% to 8%, such as 3% to 5%," is intended to encompass ranges of "1% to 8%," "1% to 5%," "2% to 10%," and so on. All numbers, amounts, ranges, etc., are intended to be modified by the term "about," whether or not so expressly stated. Similarly, a range given of "about 1% to 10%" is intended to have the term "about" modifying both the 1% and the 10% endpoints. Further, it is understood that when an amount of a component is given, it is intended to signify the amount of the active material unless otherwise specifically stated.

Notwithstanding that the numerical ranges and parameters setting forth the broad scope of the disclosure are approximations, unless otherwise indicated the numerical values set forth in the specific examples are reported as precisely as possible. Any numerical value, however, inherently contains certain errors necessarily resulting from the standard deviation found in their respective testing measurements. The examples serve to illustrate embodiments of the present disclosure without, however, being limiting in nature.

All publications and patent applications cited in this specification are herein incorporated by reference, and for any and all purposes, as if each individual publication or patent application were specifically and individually indicated to be incorporated by reference. In the event of an inconsistency between the present disclosure and any publications or patent application incorporated herein by reference, the present disclosure controls.

What is claimed is:

1. A skin care composition, comprising:
an emulsion including:
a water phase including:
i. an active ingredient combination comprising azelaic acid present in a range from about 0.5% to about 5%, at least one hydroquinone derivative present in a range from about 0.5% to about 5%, and niacinamide present in a range from about 0.5% to about 4.0%, all amounts by weight, based on the total weight of the skin care composition; and
an oil phase including:
ii. at least one anionic polymer thickener; and
iii. at least one fatty compound,
wherein:
the emulsion is a temperature-stable gel-stabilized emulsion;
the skin care composition is free of monoalcohols, other than hydroxyacetophenone, at concentrations of 0.1% or greater, by weight based on the total weight of the skin care composition;
the skin care composition is free of oils at concentrations of 0.1% or greater, by weight based on the total weight of the skin care composition, other than squalene, isononyl isononanoate, hydrogenated polyisobutene, or combinations thereof;
the skin care composition is free of silicones at concentrations of 0.1% or greater, by weight based on the total weight of the skin care composition; and
the skin care composition is free of silicone oils at concentrations of 0.1% or greater, by weight based on the total weight of the skin care composition.

2. The skin care composition according to claim 1, wherein: the at least one hydroquinone derivative is alpha arbutin.

3. The skin care composition according to claim 1, wherein: the at least one anionic polymer comprises ammonium polyacryloyldimethyl taurate and hydroxyethyl acrylate/sodium acryloyldimethyl taurate copolymer.

4. The skin care composition according to claim 1, wherein: the at least one fatty compound comprises hydrogenated polyisobutene, isononyl isononanoate, and squalane.

5. The skin care composition according to claim 1, wherein:
the skin care composition is free of silicones; and
the skin care composition is free of silicone oils.

6. The skin care composition according to claim 1, wherein the skin care composition is stable at 45° C. for a period of eight weeks, stability evidenced by a lack of phase separation, a lack of crystal formation, or a combination thereof.

7. The skin care composition according to claim 1, further comprising additional components that include one or more water-soluble solvents, humectants, other actives, preservatives, pH adjusters, chelating agents, pigments, fragrance, or any combinations thereof.

8. The skin care composition according to claim 1, wherein azelaic acid is present in a range from about 0.5% to about 4.5%, based on the total weight of the skin care composition.

9. The skin care composition according to claim 1, wherein the at least one hydroquinone derivative is present in a range from about 0.5% to about 4.5%, by weight, based on the total weight of the skin care composition.

10. The skin care composition according to claim 1, wherein niacinamide is present in a range from about 0.5% to about 3.5%, by weight, based on the total weight of the skin care composition.

11. The skin care composition according to claim 1, wherein the at least one anionic polymer is present in a range from about 0.05% to about 3%, by weight, based on the total weight of the skin care composition.

12. The skin care composition according to claim 1, wherein the total amount of anionic polymer is present in a range from about 0.5% to about 3%, by weight, based on the total weight of the skin care composition.

13. The skin care composition according to claim 1, wherein the at least one anionic polymer comprises one or more of ammonium polyacryloyldimethyl taurate, hydroxyethyl acrylate/sodium acryloyldimethyl taurate copolymer, or a combination thereof.

14. The skin care composition according to claim 1, wherein the at least one fatty compound is present in a range from about 1% to about 15%, by weight, based on the total weight of the skin care composition.

15. The skin care composition according to claim 1, wherein the at least one fatty compound comprises one or more of hydrogenated polyisobutene, isononyl isononanoate, squalane, or a combination thereof.

16. A skin care composition, comprising:
an emulsion comprising:
a water phase including:
a combination of actives that include azelaic acid, at least one hydroquinone derivative, and niacinamide; and
an oil phase including:
at least one anionic polymer thickener; and
at least one fatty compound,
wherein:
the skin care composition is free of oils at concentrations of 0.1% or greater, by weight based on the total weight of the skin care composition, other than squalene, isononyl isononanoate, hydrogenated polyisobutene, or combinations thereof;
the skin care composition is free of monoalcohols, other than hydroxyacetophenone, at concentrations of 0.1% or greater, by weight based on the total weight of the skin care composition;
the azelaic acid is present in a range from about 0.5% to about 5%;
the at least one hydroquinone derivative is present in a range from about 0.5% to about 5%;
the niacinamide is present in a range from about 0.5% to about 4%;
the at least one anionic polymer is present in a range from about 0.05% to about 3%;
the at least one fatty compound is present in a range from about 1% to about 15%; and
all amounts by weight based on the total weight of the skin care composition, wherein the skin care composition is free of silicone oils, and wherein the emulsion is a gel-stabilized emulsion.

17. The skin care composition according to claim 16, wherein: the azelaic acid is present in a range from about 3% to about 5%; the at least one hydroquinone derivative is present in a range from about 2% to about 5%; niacinamide is present in a range from about 2.5 to about 3.5%; the at least one anionic polymer is present in a range from about 1.5% to about 3%; and the at least one fatty compound is present in a range from about 5% to about 10%, all amounts by weight based on the total weight of the skin care composition.

18. The skin care composition according to claim 16, wherein: the at least one hydroquinone derivative is alpha arbutin; the at least one anionic polymer comprises ammonium polyacryloyldimethyl taurate and hydroxyethyl acrylate/sodium acryloyldimethyl taurate copolymer; and the at least one fatty compound comprises hydrogenated polyisobutene, isononyl isononanoate, and squalane, and wherein the skin care composition further comprises a blend of botanical extracts, glycerin, propylene glycol, and silica silylate, and wherein the skin care composition is stable at 45° C. for a period of eight weeks, and demonstrates stability for 10 freeze-thaw cycles at −20° C./25° C., stability evidenced by a lack of phase separation.

\* \* \* \* \*